United States Patent
Kurosaki et al.

(10) Patent No.: US 11,369,778 B2
(45) Date of Patent: Jun. 28, 2022

(54) BALLOON CATHETER AND MANUFACTURING METHOD THEREOF, AND TREATMENT METHOD

(71) Applicant: TERUMO KABUSHIKI KAISHA, Tokyo (JP)

(72) Inventors: Yasuo Kurosaki, Kanagawa (JP); Katsumi Morimoto, Kanagawa (JP); Yu Murata, Kanagawa (JP); Hiroshi Goto, Ashigarakami-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 668 days.

(21) Appl. No.: 15/467,304

(22) Filed: Mar. 23, 2017

(65) Prior Publication Data
US 2017/0274187 A1    Sep. 28, 2017

(30) Foreign Application Priority Data

Mar. 23, 2016 (JP) .............................. JP2016-058030

(51) Int. Cl.
*A61M 25/10* (2013.01)
*B05D 1/42* (2006.01)
(Continued)

(52) U.S. Cl.
CPC ........... *A61M 25/10* (2013.01); *A61K 31/337* (2013.01); *A61K 31/436* (2013.01); *A61L 29/16* (2013.01);
(Continued)

(58) Field of Classification Search
CPC .......... A61M 25/10; A61M 2025/1031; A61M 2025/105; A61M 2025/1081;
(Continued)

(56) References Cited

U.S. PATENT DOCUMENTS 8,951,545 B2   2/2015   Arps et al.
9,061,127 B2   6/2015   Weber et al.
(Continued)

FOREIGN PATENT DOCUMENTS

EP   2 271 379 B1   11/2015
EP   2 944 331 A1   11/2015
(Continued)

OTHER PUBLICATIONS

U.S. Appl. No. 15/467,002, filed Mar. 23, 2017.
(Continued)

*Primary Examiner* — Brandy S Lee
(74) *Attorney, Agent, or Firm* — Buchanan Ingersoll & Rooney PC

(57) ABSTRACT

A balloon catheter that includes an elongated main body, a balloon connected to the elongated main body, and a base layer on the outer surface of the balloon. The base layer includes a water-soluble low-molecular weight compound. The balloon catheter also includes a plurality of elongate bodies extending radially away from the outer surface of the balloon. The elongate bodies are crystals of a water-insoluble drug. The elongate bodies each possesses an independent longitudinal axis. At least part of at least some of the elongate bodies are located in the interior of the base layer on the outer surface of the balloon.

21 Claims, 7 Drawing Sheets

(51) Int. Cl.
  *A61L 29/16* (2006.01)
  *B05D 1/00* (2006.01)
  *A61K 31/337* (2006.01)
  *A61K 31/436* (2006.01)
  *A61M 25/00* (2006.01)
  *B05D 1/26* (2006.01)
  *C30B 7/06* (2006.01)
  *C30B 29/58* (2006.01)
  *C30B 29/62* (2006.01)

(52) U.S. Cl.
  CPC ...... *A61M 25/0026* (2013.01); *A61M 25/104* (2013.01); *A61M 25/1029* (2013.01); *B05D 1/002* (2013.01); *B05D 1/26* (2013.01); *B05D 1/42* (2013.01); *C30B 7/06* (2013.01); *C30B 29/58* (2013.01); *C30B 29/62* (2013.01); *A61M 2025/0039* (2013.01); *A61M 2025/105* (2013.01); *A61M 2025/1031* (2013.01); *A61M 2025/1061* (2013.01); *A61M 2025/1075* (2013.01); *A61M 2025/1086* (2013.01); *B05D 2401/20* (2013.01)

(58) Field of Classification Search
  CPC .. A61M 2025/1086; A61M 2205/0238; A61M 2025/1061; A61M 2025/1075; A61M 25/1029; B05D 1/002; B05D 1/26; B05D 1/42; B05D 2401/20; A61L 29/08; A61L 29/16; A61L 2420/06; A61L 2300/416; A61L 2300/63
  See application file for complete search history.

(56) References Cited

U.S. PATENT DOCUMENTS

| | | | |
|---|---|---|---|
| 9,168,362 B2 | 10/2015 | Morero et al. | |
| 9,198,968 B2 | 12/2015 | Michal et al. | |
| 9,901,955 B2 | 2/2018 | Kurosaki et al. | |
| 2004/0073284 A1* | 4/2004 | Bates | A61P 9/10 623/1.11 |
| 2005/0255142 A1* | 11/2005 | Chudzik | A61L 31/10 424/426 |
| 2009/0246252 A1* | 10/2009 | Arps | A61P 7/02 424/425 |
| 2011/0008260 A1* | 1/2011 | Flanagan | A61P 35/00 424/9.3 |
| 2014/0271775 A1 | 9/2014 | Cleek et al. | |
| 2014/0358122 A1* | 12/2014 | Yamashita | A61M 25/10 604/509 |
| 2015/0182732 A1 | 7/2015 | Zeng et al. | |
| 2015/0328441 A1 | 11/2015 | Stroud et al. | |
| 2016/0008522 A1 | 1/2016 | Yamashita et al. | |
| 2016/0015864 A1 | 1/2016 | Yamashita et al. | |
| 2016/0213890 A1* | 7/2016 | Kaufman | A61L 29/16 |
| 2017/0274185 A1 | 9/2017 | Morimoto et al. | |
| 2017/0274186 A1 | 9/2017 | Kurosaki et al. | |
| 2018/0147600 A1 | 5/2018 | Kurosaki et al. | |

FOREIGN PATENT DOCUMENTS

| | | |
|---|---|---|
| EP | 2 944 332 B1 | 8/2016 |
| JP | 2012-502690 A | 2/2012 |
| JP | 2015-42280 A | 3/2015 |
| WO | 03/047508 A2 | 6/2003 |
| WO | 2007/030512 A2 | 3/2007 |
| WO | 2009/051614 A1 | 4/2009 |
| WO | 2009120361 A2 | 10/2009 |
| WO | 2014/163092 A1 | 10/2014 |
| WO | 2014/163093 A1 | 10/2014 |
| WO | WO 2014/163091 A1 | 10/2014 |
| WO | 2015/151876 A1 | 10/2015 |
| WO | WO 2015/181826 A1 | 12/2015 |
| WO | 2017/164278 A1 | 9/2017 |
| WO | WO-2017/164278 A1 | 9/2017 |

OTHER PUBLICATIONS

U.S. Appl. No. 15/467,140, filed Mar. 23, 2017.
The extended European Search dated Aug. 8, 2019, by the European Patent Office in corresponding European Patent Application No. 17770318.8-1132. (6 pages).
International Search Report dated Jun. 20, 2017, by the Japan Patent Office in International Application No. PCT/JP2017/011631 and English translation of the Search Report (4 pages).
Office Action (Communication pursuant to Article 94(3) EPC) dated Nov. 16, 2020 by the European Patent Office in corresponding European Patent Application No. 17 770 318.8-1132. (4 pages).
Office Action (First Office Action) dated Jun. 24, 2020, by the State Intellectual Property Office of People's Republic of China in corresponding Chinese Patent Application No. 201780019565.6 and an English Translation of the Office Action. (18 pages).

* cited by examiner

BALLOON CATHETER AND MANUFACTURING METHOD THEREOF, AND TREATMENT METHOD

CROSS-REFERENCES TO RELATED APPLICATIONS

This application claims priority to Japanese Application No. 2016-058030 filed on Mar. 23, 2016, the entire content of which is incorporated herein by reference.

BACKGROUND

The present disclosure generally relates to a balloon catheter provided with a crystalline drug on an outer surface of a balloon, a balloon catheter manufacturing method, and a treatment method using the balloon catheter.

In recent years, balloon catheters have been used for improving lesion affected areas (stenosed parts) in body lumens. A balloon catheter normally includes an elongated shaft portion and a balloon on the distal side of the shaft portion. The balloon is inflatable/deflatable in the radial direction. After the balloon is brought to a target site in the body by way of a thin body lumen while the balloon is in a deflated state, the balloon is inflated, whereby the lesion affected area can be pushed wide open (i.e., widened).

If a lesion affected area is forcibly pushed wide open, however, excessive proliferation of smooth muscle cells may occur, causing new stenosis (restenosis) at the lesion affected area. In view of this possible restenosis problem, drug eluting balloons (DEBs) have recently been used. Drug eluting balloons possess a balloon with an outer surface that is coated with a drug for restraining stenosis. The drug eluting balloon is able to instantaneously release the drug contained in the coating on the outer surface of the balloon to the lesion affected area and deliver the drug to the living body tissue by being inflated, thereby restraining restenosis.

In recent years, it has been becoming clear that the morphological form of the drug in the coating on the balloon outer surface influences the releasing property of the drug from the balloon surface and/or the tissue transferability of the drug at the lesion affected area. For instance, U.S. Patent Application Publication No. 2014/0271775 describes a balloon catheter wherein crystals of a drug are formed in elongate form on an outer surface of a balloon.

SUMMARY

For enhancing a therapeutic effect, a drug eluting balloon catheter is desirably configured in such a manner that the drug on the outer surface of the balloon is highly deliverable (i.e., relatively easily transferable) to living body tissue and that the deliverability can be controlled.

The balloon catheter disclosed here permits a drug to be effectively delivered to living body tissue and for the deliverability to be controlled. The manufacturing method of the balloon catheter and the treatment method using the balloon catheter also permit the drug to be effectively delivered and for the deliverability to be controlled.

In one aspect of the present disclosure, there is provided a balloon catheter that includes a balloon with a plurality of elongate bodies on the outer surface of the balloon. The plurality of elongate bodies are crystals of a water-insoluble drug extending while having independent long axes (i.e., longitudinal axes). The balloon catheter includes a base layer having a water-soluble low-molecular weight compound disposed in a layer form on the outer surface of the balloon. At least part of the elongate bodies is located in the inside of the base layer.

The balloon catheter configured as described above is characterized in that inflation of the balloon causes cracking of the base layer, which facilitates dissolution of the base layer. This dissolution enables the elongate bodies (i.e., that are the drug crystals) to be easily released from the base layer, so that the drug can be effectively delivered to living body tissue. Furthermore, when the base layer including the water-soluble low-molecular weight compound is dissolved gradually or rapidly, the elongate bodies in the inside of the base layer make contact with the living body tissue and the drug is thereby delivered to the living body tissue. Therefore, the deliverability of the drug can be controlled by the material and by the thickness of the base layer and the positions of the elongate bodies relative to the base layer.

The elongate bodies may include first elongate bodies which possess proximal portions that are separate from the outer surface of the balloon and are located in the inside of the base layer. In this configuration, the deliverability of the drug to living body tissue can be controlled through utilization of the time taken for dissolution of the base layer including the water-soluble low-molecular weight compound by adjusting the positions of the proximal portions of the first elongate bodies to be in the inside of the base layer.

The elongate bodies may include second elongate bodies extending from the outer surface of the balloon. The second elongate bodies can be eluted from the base layer slowly as the base layer is dissolved, and the drug can be slowly delivered to the living body tissue.

The elongate bodies may include third elongate bodies extending from an outer surface of the base layer toward the outside of the surface. In this case, the third elongate bodies immediately make collective contact with the living body tissue, so that the drug can be instantaneously delivered to the living body tissue.

The water-insoluble drug may be rapamycin, paclitaxel, docetaxel, or everolimus. Using these drugs can favorable inhibit restenosis of a stenosed part in a blood vessel by the elongate bodies of which at least part is located in the inside of the base layer.

In another aspect of the present disclosure, there is provided a method of coating a balloon catheter including causing a balloon catheter to contact a dispensing tube, the balloon catheter including an elongated tubular body which possesses a distal portion, the balloon being attached to the distal portion of the elongated tubular body, the balloon possessing an outer surface that contacts the dispensing tube; applying a coating solution containing a water-insoluble drug, a water-soluble low-molecular weight compound, an organic solvent, and water from the dispensing tube onto the outer surface of the balloon of the balloon catheter, the coating solution being applied by the dispensing tube while keeping the dispensing tube in contact with the outer surface of the balloon; giving a physical stimulus to the coating solution to cause formation of crystal nuclei of the water-insoluble drug while applying the coating solution with the dispensing tube; volatilizing the organic solvent while leaving the water to cause growth of the elongate bodies based on the crystal nuclei; and evaporating the water to form a base layer on the outer surface of the balloon, the base layer including the water-soluble low-molecular weight compound.

According to the method of manufacturing a balloon catheter configured as above, volatilization of the organic solvent from the layer including the water-soluble low-molecular weight compound containing water leads to growth of drug crystals from the crystal nuclei, whereby elongate bodies of which at least part is located in the interior of the base layer can be formed.

In a further aspect of the present disclosure, there is provided a treatment method for delivering a drug to a lesion affected area in a body lumen. The treatment method including: introducing a balloon catheter into the living body, the balloon catheter comprising an elongated tubular body, a balloon attached to a distal portion of the elongated tubular body, a base layer comprising a water-soluble low-molecular weight compound located on an outer surface of the balloon and a plurality of elongate bodies extending radially outward through at least part of the base layer, the elongate bodies being crystals of a water-insoluble drug; moving the balloon catheter within the living body into the body lumen to position the balloon of the balloon catheter at the lesion affected area; inflating the balloon to press the balloon against living body tissue of the lesion affected area, the inflating of the balloon causing the elongate bodies to contact the living body tissue; dissolving the base layer including the water-soluble low-molecular weight compound; deflating the balloon; and withdrawing the balloon catheter out of the living body while the balloon is deflated.

According to the treatment method configured as above, inflation of the balloon causes cracking of the base layer, which facilitates dissolution of the base layer, thereby enabling the elongate bodies as the drug crystals to be easily released from the base layer, so that the drug can be effectively delivered to living body tissue. Furthermore, during when the base layer including the water-soluble low-molecular weight compound is dissolved gradually or rapidly, the elongate bodies in the inside of the base layer make contact with the living body tissue and the drug is thereby delivered to the living body tissue. Therefore, the deliverability of the drug can be controlled by the material and thickness of the base layer and the positions of the base portions of the elongate bodies relative to the base layer.

DETAILED DESCRIPTION OF THE PREFERRED EMBODIMENT

Figure 1:
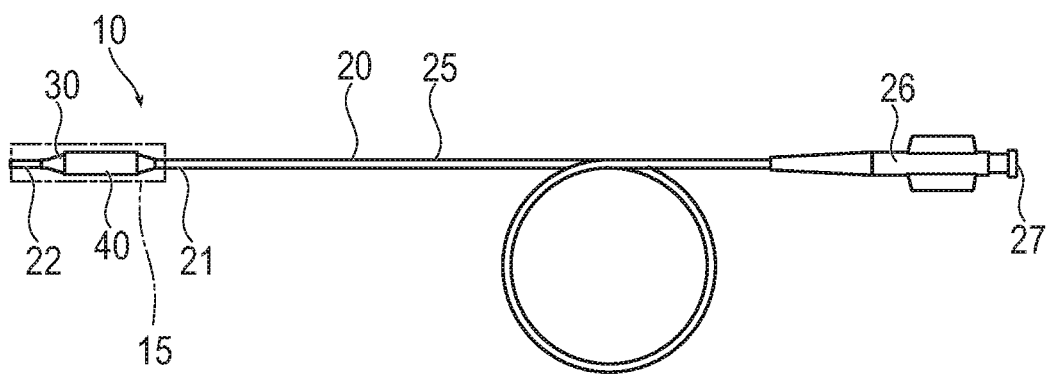
FIG. 1 is a front view of an embodiment of a balloon catheter.

Set forth below with reference to the accompanying drawings is a detailed description of embodiments of a balloon catheter, a balloon catheter manufacturing method and a treatment method representing examples of the inventive balloon catheter, balloon catheter manufacturing method and treatment method disclosed here. Note that for convenience of explanation/illustration, the dimensional ratios in the drawings may be exaggerated and different from the actual ratios.

Figure 2:
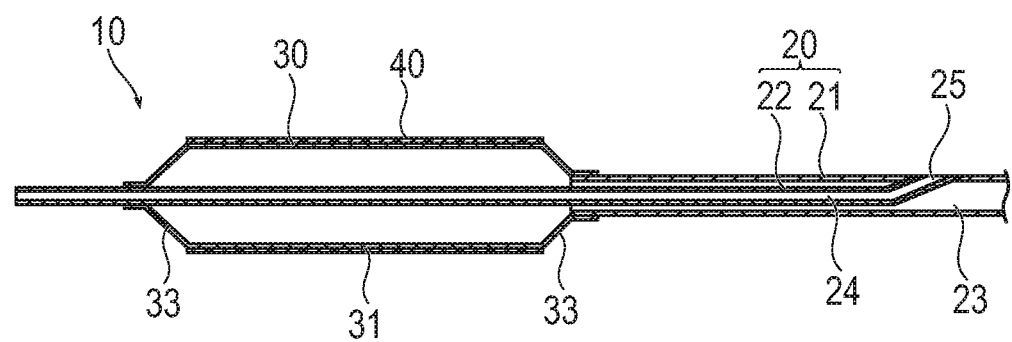
FIG. 2 is a sectional view of a distal portion of the balloon catheter.

As shown in FIGS. 1 and 2, a balloon catheter 10 according to an embodiment of the present disclosure is a drug eluting type catheter with crystals of a drug provided on an outer surface of a balloon 30. Note that in this disclosure, the side on which the balloon catheter 10 is inserted into a body lumen will be referred to as "distal end" or "distal side," while the operator's hand side on which the balloon catheter 10 is operated will be referred to as "proximal end" or "proximal side."

First, the structure of the balloon catheter 10 will be described. The balloon catheter 10 includes an elongated catheter main body 20, the balloon 30 provided on a distal portion of the catheter main body 20, a drug-containing coating layer 40 provided on the outer surface of the balloon 30, and a hub 26 attached to a proximal end of the catheter main body 20. The balloon 30 with the coating layer 40 is covered and protected with a protective sheath 15 until put to use (e.g., inflated at the lesion site).

The catheter main body 20 includes an outer tube 21 and an inner tube 22 which is a tube body disposed inside the outer tube 21. The outer tube 21 is a tubular body that is open at the distal and proximal ends. The inner tube 22 is accommodated in a hollow (i.e., an annular space or lumen) inside of the outer tube 21. The distal portion of the catheter main body 20 is a double tube structure. The hollow inside of the inner tube 22 is a guide wire lumen 24 for passing a guide wire therethrough (i.e., a guide wire is positionable in or insertable through the guide wire lumen 24). In the hollow inside of the outer tube 21 and on the outside of the inner tube 22, there is an inflation lumen 23. An inflation fluid for inflating the balloon 30 may pass through the inflation lumen 23. The inner tube 22 is open to the exterior (i.e., surrounding environment) at an opening portion 25. The inner tube 22 protrudes distally beyond the distal end of the outer tube 21.

A proximal-side end portion of the balloon 30 is fixed to the outer surface of the outer tube 21 at a distal portion of the outer tube 21 as illustrated in FIG. 2. A distal-side end portion of the balloon 30 is fixed to the outer surface of the inner tube 21 at a distal portion of the inner tube 22 as illustrated in FIG. 2. This configuration results in the inside of the balloon 30 communicating with the inflation lumen 23. The balloon 30 can thus be inflated by injecting the inflation fluid through the inflation lumen 23 and into the balloon 30. The inflation fluid may be a gas or a liquid. For example, gases such as helium gas, $CO_2$ gas, $O_2$ gas, etc. and liquids such as physiological saline solution, a contrast agent, etc. can be used as the inflation fluid.

At a central portion in the axial direction of the balloon 30, there is a hollow cylindrical straight portion 31 (inflatable portion) having an equal outer diameter when inflated. Tapered portions 33 (where the outer diameter gradually varies) are formed on both sides of the straight portion 31 in the axial direction. The coating layer 40 (which contains a drug) is formed on the whole part of the outer surface of the straight portion 31 (i.e., the entirety of the outer surface of the straight portion 31). The range of the balloon 30 in which the coating layer 40 is applied is not limited to only the straight portion 31. The range of the coating layer 40 application may include at least part of the tapered portions 33 in addition to the straight portion 31, or may include only part of the straight portion 31 (i.e., less than the entirety of the outer surface of the straight portion 31).

The hub 26 is formed with a proximal opening portion 27 that communicates with the inflation lumen 23 of the outer tube 21. The proximal opening portion 27 functions as a port through which the inflation fluid flows in and out.

The length in the axial direction of the balloon 30 is not particularly limited, and is preferably 5 to 500 mm, more preferably 10 to 300 mm, and still more preferably 20 to 200 mm.

The outer diameter of the balloon 30 when the balloon 30 is inflated is not particularly limited, and is preferably 1 to 10 mm, and more preferably 2 to 8 mm.

The outer surface of the balloon 30 is smooth and non-porous before the formation of the coating layer 40. The outer surface of the balloon 30 before the formation of the coating layer 40 may also be provided with minute holes that do not pierce through the film of the balloon 30. Alternatively, the outer surface of the balloon 30 may have both a range of being smooth and non-porous and a range of having minute holes that do not pierce through the film of the balloon 30 before the formation of the coating layer 40. The minute holes may be sized to have, for example, a diameter of 0.1 to 5 µm and a depth of 0.1 to 10 µm. One or more minute holes may be provided per crystal. Alternatively, the minute holes may be sized to have, for example, a diameter of 5 to 500 µm and a depth of 0.1 to 50 µm, and one or more crystals may be provided per hole.

The balloon 30 preferably has a certain degree of flexibility and a certain degree of hardness such that the drug can be released from the coating layer 40 on the outer surface of the balloon 30 when the balloon 30 is inflated at a blood vessel or tissue or the like. Specifically, the balloon 30 is formed from metal or resin. It is preferable that at least the outer surface of the balloon 30 that the coating layer 40 is applied to is formed of resin. Examples of the material which can be used for forming at least the outer surface of the balloon 30 include thermoplastic resins such as polyolefins (e.g., polyethylene, polypropylene, polybutene, ethylene-propylene copolymers, ethylene-vinyl acetate copolymers, ionomers, or mixtures of two or more of them), flexible polyvinyl chloride resin, polyamides, polyamide elastomers, nylon elastomers, polyester, polyester elastomers, polyurethane, fluororesins, etc., silicone rubbers, and latex rubbers. Among these, the polyamides are preferable. Specifically, at least part of the outer surface of the balloon 30 to be coated with the drug is preferably made of a polyamide. The polyamide is not particularly limited so long as the polyamide is a polymer which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., and aromatic polyamides such as copolymers of adipic acid with metaxylenediamine, or copolymers of hexamethylenediamine with m,p-phthalic acid. Further, polyamide elastomers as block copolymers wherein nylon 6, nylon 66, nylon 11, nylon 12 or the like constitutes hard segments and a polyalkylene glycol, a polyether, an aliphatic polyester or the like constitutes soft segments can also be used as a material of the balloon 30. The above-mentioned polyamides may be used either singly or in combination of two or more polyamides.

Figure 3:
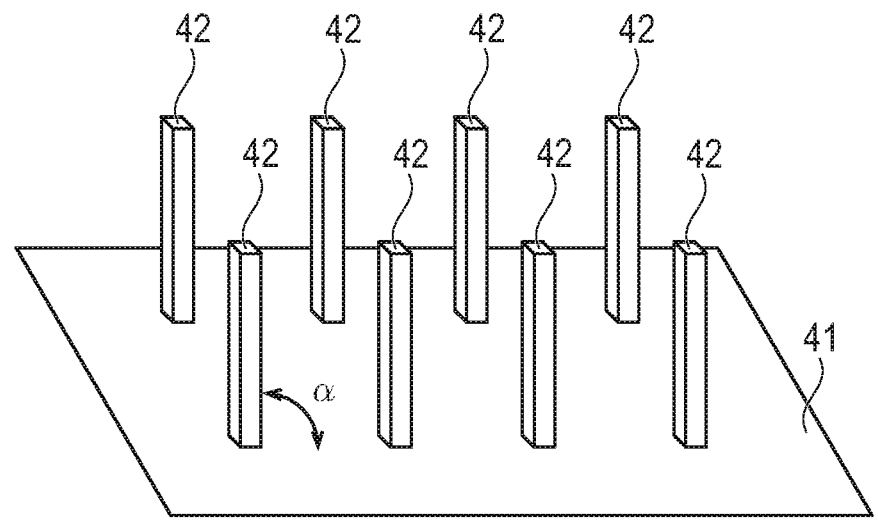
FIG. 3 is a schematic perspective view of elongate bodies consisting of drug crystals on an outer surface of a balloon.
Figure 4:
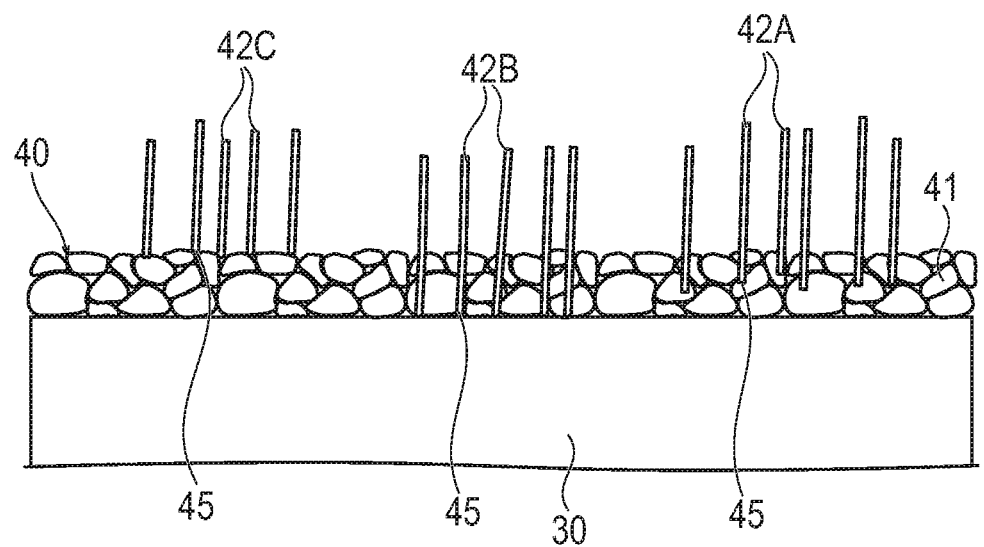
FIG. 4 is a schematic view showing the elongate bodies, consisting of the drug crystals, and a base layer on the outer surface of the balloon.

The coating layer 40 is formed on the outer surface of the balloon 30 either directly or through a pre-treatment layer such as a primer layer between the coating layer 40 and the outer surface of the balloon 30. The method of applying the coating layer 40 on the outer surface of the balloon 30 will be described later. As shown in FIGS. 3 and 4, the coating layer 40 includes a base layer 41 (excipient). The base layer 41 is an additive layer including a water-soluble low-molecular weight compound disposed in a layer form on the outer surface of the balloon 30. The coating layer 40 also includes a plurality of elongate bodies 42 which are crystals of a water-insoluble drug having independent long axes and extending along the long axes (i.e., the elongate bodies 42 each possess a longitudinal axis that extends/protrudes towards the surrounding environment from the outer surface of the balloon 30 and/or from the coating layer 40). Each of the elongate bodies 42 may be independently formed from one another (i.e., from the tip of the elongate body 42 to the base of the elongate body 42) and may be spaced apart to not contact any of the adjacent elongate bodies 42 as illustrated in FIG. 3. The long axes (longitudinal axes) of the elongate bodies 42 may be substantially linear (i.e., linearly-shaped) as also shown in FIG. 3. The plurality of elongate bodies 42 may be acicular (needle-shaped). The elongate bodies 42 include first elongate bodies 42A extending from the inside of the base layer 41 to the outside of the base layer 41 (i.e., the first elongate bodies 42A extend from the interior of the base layer 41 to protrude beyond the base layer), second elongate bodies 42B extending from the outer surface of the balloon 30 to the outside of the base layer 41 by penetrating through the base layer 41, and third elongate bodies 42C extending directly from the outer surface of the base layer 41 to the outside of the surface (i.e., not penetrating into the interior of the base layer 41). In other words, base portions 45 of the elongate bodies 42 may directly contact the outer surface of the balloon 30, or may not directly contact the outer surface of the balloon 30 because an excipient constituting the base layer 41 is present between the base portions 45 and the outer surface of the balloon 30. The plurality of elongate bodies 42 may be regularly disposed (i.e., uniformly or in a pattern) on the outer surface of the balloon 30. Alternatively, the plurality of elongate bodies 42 may be irregularly disposed (non-uniformly) on the outer surface of the balloon 30. The elongate bodies 42A, 42B, and 42C differ from one another in the deliverability of the drug to a living body tissue. Therefore, the deliverability of the drug can be controlled by regulating the positions of the base portions 45 of the crystals of the drug. The coating layer 40 may be prepared so that almost only the elongate bodies 42A exist on the outer surface of the balloon 30. The coating layer 40 may be prepared so that almost only the elongate bodies 42B exist on the outer surface of the balloon 30. The coating layer 40 may be prepared so that almost only the elongate bodies 42C exist on the outer surface of the balloon 30. Alternatively, the coating layer 40 may be prepared so that a combination of a plurality of types of elongate bodies 42A, 42B and/or 42C exists on the outer surface of the balloon 30. Examples of such combination include a combination of the elongate bodies 42A with the elongate bodies 42B, a combination of the elongate bodies 42B with the elongate bodies 42C, and a combination of the elongate bodies 42C with the elongate bodies 42A. The coating layer 40 may be prepared so that all of the elongate bodies 42A, 42B, and 42C exist on the outer surface of the balloon 30 as illustrated in FIG. 4.

The inclination angle α of the long axes of the elongate bodies 42 relative to the outer surface of the balloon 30 or the base layer 41 is not particularly limited, and the inclination angle α is 45 to 135 degrees, preferably 60 to 120 degrees, more preferably 75 to 105 degrees, and still more preferably approximately 90 degrees.

The amount of the drug contained in the coating layer 40 is not particularly limited. The density amount of the drug contained in the coating layer 40 is 0.1 to 10 µg/mm$^2$, preferably 0.5 to 5 µg/mm$^2$, more preferably 0.5 to 3.5 µg/mm$^2$, and still more preferably 1.0 to 3 µg/mm$^2$. The amount of the crystals in the coating layer 40 is not particularly limited, and is preferably 5 to 500,000 crystals/(10 µm$^2$), more preferably 50 to 50,000 crystals/(10 µm$^2$), and still more preferably 500 to 5,000 crystals/(10 µm$^2$).

The plurality of elongate bodies 42 wherein the crystals have mutually independent long axes may also be present in a state where they are combined. The plurality of adjacent elongate bodies 42 may be in contact with one another while forming different angles relative to each other. The plurality of elongate bodies 42 may be positioned so that there are spaces (spaces in which the crystal is not contained) between the elongate bodies 42 on the outer surface of the balloon 30. Both a plurality of elongate bodies 42 in a combined state (i.e., some of the elongate bodies 42 contact one another) and a plurality of elongate bodies 42 in a separate and independent state may exist on the surface of the balloon 30. The plurality of elongate bodies 42 may be arranged in a circumferential and brush-like pattern while having different long axis directions. The elongate bodies 42 each exist independently, each possess a certain length, and each include one end (proximal end) in the longitudinal direction (extending direction) that is fixed to the base layer 41 or fixed to the outer surface of the balloon 30. The elongate body 42 does not form a composite structure, and is not interlocked, with the adjacent elongate bodies 42. The long axes of the crystals are almost rectilinear. The elongate bodies 42 form predetermined angles relative to the surface which their long axes intersect and with which their base portions 45 make contact.

The elongate bodies 42 preferably extend independently from one another, without making contact with one another. The base portions 45 of the elongate bodies 42 may be in contact with other base portions 45 of adjacent elongate bodies 42 on the substrate of the balloon 30. The base portions 45 of the elongate bodies 42 may also be independent from the base portions 45 of the adjacent elongate bodies 42 so that the base portions 45 of the elongate bodies 42 do not contact other base portions 45 on the substrate of the balloon 30.

The elongate bodies 42 may be hollow (i.e., contain a space in the interior of the elongate body 42) or may be solid. Both hollow elongate bodies 42 and solid elongate bodies 42 may exist on the surface of the balloon 30. At least a portion of the elongate body 42 near the distal end of the elongate body 42 may be hollow. A section of the elongate body 42 in a plane perpendicular (orthogonal) to the long axis of the elongate body 42 may have a void (hollow portion). In the elongate body 42 thus having a void, the section of the elongate body 42 in a plane perpendicular (orthogonal) to the long axis is polygonal in shape. The polygon here is, for example, a triangle, a tetragon, a pentagon, or a hexagon. Therefore, the elongate bodies 42 are each formed as an elongate polyhedron with a distal end (or a distal surface) and a proximal end (or a proximal surface) and in which a side surface portion between the distal end (or the distal surface) and the proximal end (or the proximal surface) is composed of a plurality of substantially planar surfaces. This crystalline morphological form (hollow elongate body crystalline morphological form) constitutes the whole part or at least part of a plane, at the surface with which the base portions 45 make contact.

The length in the long axis direction of the elongate bodies 42 having the long axes is preferably 5 to 20 µm, more preferably 9 to 11 µm, and still more preferably around 10 µm. The diameter of the elongate bodies 42 having the long axes is preferably 0.01 to 5 µm, more preferably 0.05 to 4 µm, and still more preferably 0.1 to 3 µm. Examples of the combination of length in the long axis direction and diameter of the elongate bodies 42 having the long axes include a combination of a diameter of 0.01 to 5 µm when the length is 5 to 20 µm, a combination of a diameter of 0.05 to 4 µm when the length is 5 to 20 µm, and a combination of a diameter of 0.1 to 3 µm when the length is 5 to 20 µm. The elongate bodies 42 may be rectilinear in the long axis direction of the elongate bodies 42, and may also be curved in curved line forms (i.e., curved elongate bodies 42). Both rectilinear elongate bodies 42 and curved elongate bodies 42 may exist in the coating layer 40 on the outer surface of the balloon 30.

The drug crystals of the crystalline morphological form having the long axes as described above account for at least 50% by volume, and more preferably at least 70% by volume, of the drug crystals on the outer surface of the balloon 30. The elongate bodies 42 (i.e., the crystal particles having the long axes) are formed not to lie flat but to stand (i.e., extend or protrude) relative to the outer surface of the balloon 30 or the base layer 41. The base layer 41 may exist in a region where the elongate bodies 42 are present and may not exist in a region where the elongate bodies 42 are absent.

The base layer 41 is present in the state of being distributed into spaces between the plurality of elongate bodies 42 standing together. In other words, spaces between the plurality of elongate bodies 42 may be filled by the base layer 41. In regard of the proportions of the materials constituting the coating layer 40, the crystals of the water-insoluble drug preferably occupy a larger volume than the volume occupied by the base layer 41. The excipient constituting the base layer 41 does not form a matrix. The matrix is a layer which is configured by continuation of a comparatively high-molecular material (e.g., a polymer or the like), which forms a network-like three-dimensional structure, and in which minute spaces are present. The water-insoluble drug constituting the crystals is thus not adhered to the inside of a matrix material. Moreover, the water-insoluble drug constituting the crystals is not embedded in a matrix material.

The base layer 41 is applied in an aqueous solution state to the outer surface of the balloon 30 and dries into a dried base layer 41. The base layer 41 is amorphous. The base layer 41 may be formed of crystal particles. The base layer 41 may exist as a mixture of an amorphous state with crystal particles. The base layer 41 illustrated in FIG. 4 is in a state including crystal particles and/or particulate amorphous portions. The base layer 41 is formed as a layer including the water-insoluble drug. Alternatively, the base layer 41 may be formed as an independent layer that does not include the water-insoluble drug. The thickness of the base layer 41 is 0.1 to 5 μm, preferably 0.3 to 3 μm, and more preferably 0.5 to 2 μm.

The layer including the morphological form of the elongate body crystals is low in toxicity and high in stenosis inhibitory effect at the time of delivery into a body. The water-insoluble drug including the hollow elongate body crystalline morphological form has properties promoting penetration into tissue because of a small crystal unit size upon transfer of the drug to the tissue. Since the drug has good solubility, it acts effectively and can inhibit stenosis. In addition, the drug is considered to be less liable (likely) to remain in the tissue as large lumps (i.e., in a relatively large lump form) and, therefore, shows low toxicity.

The layer including the elongate body crystalline morphological form has a plurality of substantially uniform elongate bodies 42, and the elongate bodies 42 are substantially uniformly standing (i.e., extending or protruding) together on the surface with which their base portions 45 make contact. The size (the length in the long axis direction) of the crystals transferred to the tissue is thus as small as approximately 10 μm. For this reason, the drug uniformly acts on the lesion affected area, with an enhanced ability to penetrate into the tissue. There is also no possibility that an excess amount of the drug might remain at the affected area for an excess of time because the size of the crystals transferred is relatively small. For this reason, it is considered that the drug can show a high stenosis inhibitory effect without showing toxicity.

The drug in the coating on the outer surface of the balloon 30 may include an amorphous phase. The crystals and the amorphous phase may be disposed regularly in the coating layer 40. Alternatively, the crystals and the amorphous phase may be disposed irregularly.

The protective sheath 15 is a member for inhibiting the drug from falling off the balloon 30 (i.e., being removed from the surface of the balloon). The protective sheath 15 is removed before the expansion of the balloon 30 of the balloon catheter 10. The protective sheath 15 is formed from a flexible material. Examples of the protective sheath 15 material include thermoplastic resins such as polyolefins (e.g., polyethylene, polypropylene, polybutene, ethylene-propylene copolymers, ethylene-vinyl acetate copolymers, ionomers, or mixtures of two or more of them), flexible polyvinyl chloride resin, polyamides, polyamide elastomers, polyesters, polyester elastomers, polyurethane, fluororesins, etc., silicone rubbers, and latex rubbers.

Figure 5:
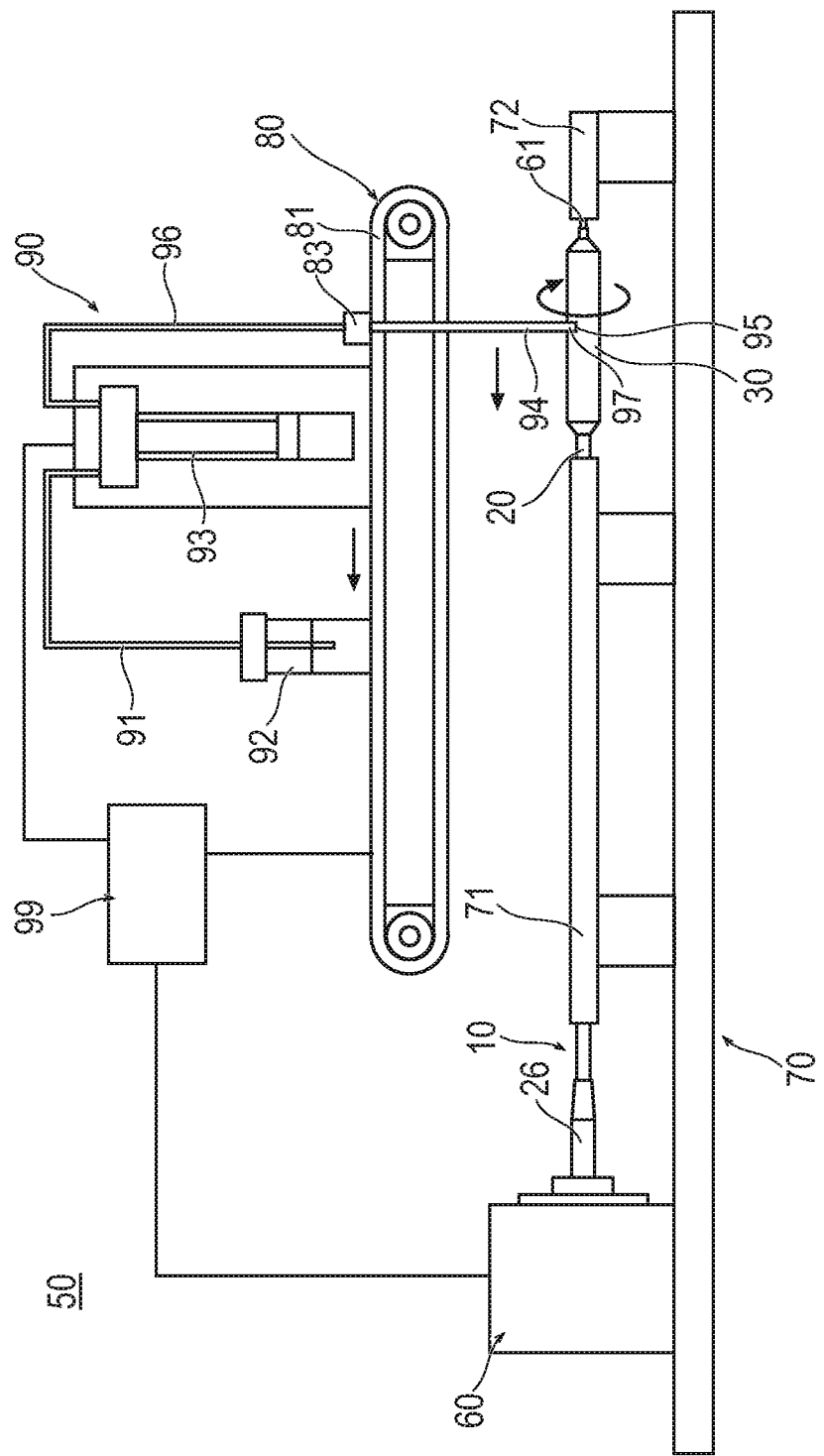
FIG. 5 is a front view of a balloon coating apparatus.
Figure 6:
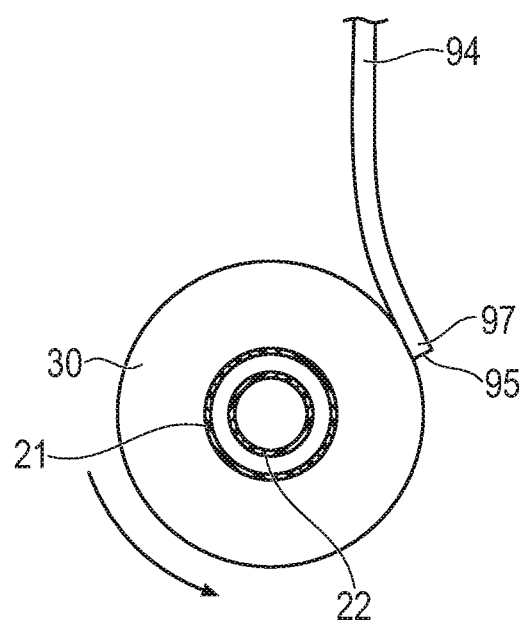
FIG. 6 is a sectional view of a dispensing tube in contact with the balloon.

A balloon coating apparatus 50 for forming the coating layer 40 on the balloon 30 will now be described. As shown in FIGS. 5 and 6, the balloon coating apparatus 50 includes a rotation mechanism section 60 (a rotation mechanism) for rotating the balloon catheter 10 and a support base 70 for supporting the balloon catheter 10. The balloon coating apparatus 50 further includes an application mechanism section 90 that includes a dispensing tube 94 for applying a coating solution to an outer surface of the balloon 30, a movement mechanism section 80 for moving the dispensing tube 94 relative to the balloon 30 (e.g., in the axial direction), and a control unit 99 for controlling the balloon coating apparatus 50.

The rotation mechanism section 60 holds the hub 26 of the balloon catheter 10 and rotates the balloon catheter 10 around an axis of the balloon 30 by a drive source, such as a motor, incorporated in the rotation mechanism section 60. The balloon catheter 10 is held with a core member 61 inserted in the guide wire lumen 24. The core member 61 helps prevent the coating solution from flowing into the guide wire lumen 24. A three-way cock capable of operating the opening/closing of a passage or passages is connected to the proximal opening portion 27 of the hub 26 for allowing a fluid to be introduced into the inflation lumen 23.

The support base 70 includes a tubular proximal-side support section 71 that accommodates the catheter main body 20 in the support section 71 and rotatably supports the catheter main body 20. The support base 70 also includes a distal-side support section 72 that rotatably supports the core member 61. The distal-side support section 72 may, if possible, rotatably support a distal portion of the catheter main body 20 instead of the core member 61.

The movement mechanism section 80 includes a movable base 81 which can be moved rectilinearly in a direction parallel to the axis of the balloon 30 (i.e., in the axial direction) and a tube fixing section 83 to which the dispensing tube 94 is fixed (i.e., held or attached). The movable base 81 can be moved rectilinearly by a drive source, such as a motor, incorporated in the movable base 80. The tube fixing section 83 fixes an upper end of the dispensing tube 94 relative to the movable base 81. The dispensing tube 94 thus moves rectilinearly in a direction parallel to the axis of the balloon 30 (i.e., in the axial direction) when the movable base 81 moves. The application mechanism section 90 is also mounted on the movable base 81, and the movable base 81 moves the application mechanism section 90 rectilinearly in both directions along the axis of the balloon 30 (i.e., proximally and distally along the axial direction of the balloon 30).

The application mechanism section 90 is a section that applies the coating solution to the outer surface of the balloon 30. The application mechanism section 90 includes a container 92 containing the coating solution, a feed pump 93 that feeds the coating solution at an arbitrary feed rate, and the dispensing tube 94 that applies the coating solution to the balloon 30.

The feed pump 93 is, for example, a syringe pump. The feed pump 93 can draw the coating solution from the container 92 through a suction tube 91 and feed the coating solution into the dispensing tube 94 through a supply tube 96 at an arbitrary feed rate based on control applied by the control unit 99. The feed pump 93 is disposed on the movable base 81 and can be moved rectilinearly by the movement of the movable base 81. The feed pump 93 is not limited to being a syringe pump so long as it can feed the coating solution. The feed pump 93 may be, for example, a tube pump.

The dispensing tube 94 is a member which communicates with the supply tube 96 and discharges the coating solution to the outer surface of the balloon 30 supplied from the feed pump 93 through the supply tube 96. The dispensing tube 94 is a flexible circular pipe-shaped member (i.e., a tubular member). The upper end of the dispensing tube 94 is fixed to the tube fixing section 83 and extends downward in the vertical direction from the tube fixing section 83. The dispensing tube 94 includes an opening portion 95 (i.e., an opening) at a discharge end 97. The discharge end is the lower end in the vertical direction as shown in FIG. 5. The dispensing tube 94 can be moved by the movable base 81 rectilinearly in both directions along the axial direction of the balloon catheter 10 (i.e., proximally and distally in the axial direction of the balloon catheter 10) together with the feed pump 93 disposed on the movable base 81. The dispensing tube 94 can supply the coating solution to the outer surface of the balloon 30 while the dispensing tube 94 is bent by being pressed against the balloon 30 as shown in FIG. 6.

The dispensing tube 94 may not necessarily possess a circular pipe-shape as long as the dispensing tube 94 can supply the coating solution. The dispensing tube 94 may additionally not necessarily extend in the vertical direction as long as the dispensing tube 94 can discharge the coating solution through the opening portion 95.

The dispensing tube 94 is preferably formed from a flexible material such that a contact burden (force) on the balloon 30 is reduced and variations in the contact position attendant on the rotation of the balloon 30 can be absorbed by flexure of the dispensing tube 94. Examples of the dispensing tube 94 material include polyolefins such as polyethylene, polypropylene, etc., cyclic polyolefins, polyesters, polyamides, polyurethane, and fluororesins such as PTFE (polytetrafluoroethylene), ETFE (tetrafluoroethylene-ethylene copolymer), PFA (tetrafluoroethylene-perfluoroalkyl vinyl ether copolymer), FEP (tetrafluoroethylene-hexafluoropropylene copolymer), etc., but the material is not particularly limited as long as the material is flexible and deformable.

The outer diameter of the dispensing tube 94 is not particularly limited. For example, the outer diameter of the dispensing tube 94 may be 0.1 to 5.0 mm, preferably 0.15 to 3.0 mm, and more preferably 0.3 to 2.5 mm. The inner diameter of the dispensing tube 94 is also not particularly limited. The inner diameter of the dispensing tube 94 may be, for example, 0.05 to 3.0 mm, preferably 0.1 to 2.0 mm, and more preferably 0.15 to 1.5 mm. The length of the dispensing tube 94 is not particularly limited and is preferably a length of not more than 5 times the balloon diameter. For example, the dispensing tube 94 length may be 1.0 to 50 mm, preferably 3 to 40 mm, and more preferably 5 to 35 mm.

The control unit 99 is composed, for example, of a computer, and unifyingly controls the rotation mechanism section 60, the movement mechanism section 80, and the application mechanism section 90. The control unit 99 can thus unifyingly control the rotating speed of the balloon 30, the moving speed of the dispensing tube 94 in the axial direction of the balloon 30, the drug discharge rate from the dispensing tube 94, and so on.

The coating solution supplied from the dispensing tube 94 to the balloon 30 is a solution or suspension containing the constituent materials of the coating layer 40. The coating solution supplied from the dispensing tube 94 contains a water-insoluble drug, an excipient, an organic solvent, and water. After the coating solution is supplied to the outer surface of the balloon 30, the organic solvent and water volatilize, whereby a coating layer 40 including a plurality of elongate bodies 42 is formed on the outer surface of the balloon 30. The plurality of elongate bodies 42 formed in this manner are crystals of the water-insoluble drug extending while having independent longitudinal axes.

The viscosity of the coating solution is 0.5 to 1,500 cP, preferably 1.0 to 500 cP, and more preferably 1.5 to 100 cP.

The water-insoluble drug means a drug which is insoluble or relatively difficultly soluble in water. Specifically, the water-insoluble drug is a drug possessing solubility in water of less than 5 mg/mL at pH 5 to 8. The solubility may be less than 1 mg/mL, or, further, may be less than 0.1 mg/mL. The water-insoluble drug includes fat-soluble drugs.

Some preferred examples of the water-insoluble drug include immunosuppressants, e.g., cyclosporines inclusive of cyclosporine, immunoadjuvants such as rapamycin, carcinostatics such as paclitaxel, antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from a group composed of rapamycin, paclitaxel, docetaxel, and everolimus. The rapamycin, paclitaxel, docetaxel, and everolimus that may be used for the water-insoluble drug include their analogs and/or derivatives as long as the analogs and/or derivatives have equivalent drug activity to the original. For example, paclitaxel and docetaxel are in an analog relation. Rapamycin and everolimus are in a derivative relation. Among these, paclitaxel is preferable.

The excipient constitutes the base layer 41 on the balloon 30. The excipient includes a water-soluble low-molecular weight compound. The molecular weight of the water-soluble low-molecular weight compound is 50 to 2,000, preferably 50 to 1,000, more preferably 50 to 500, and still more preferably 50 to 200. The amount of the water-soluble low-molecular weight compound is preferably 5 to 10,000 parts by weight, more preferably 5 to 200 parts by weight, and still more preferably 8 to 150 parts by weight, per 100 parts by weight of the water-insoluble drug. Examples of the applicable constituent material of the water-soluble low-molecular weight compound include serine ethyl esters, citric acid esters, polysorbates, water-soluble polymers, sugars, contrast agents, amino acid esters, glycerol esters of short-chain monocarboxylic acids, pharmaceutically acceptable salts and surfactants, and mixtures of two or more of these. The water-soluble low-molecular weight compound is characterized in that the water-soluble low-molecular weight compound has a hydrophilic group and a hydrophobic group and is soluble in water. The water-soluble low-molecular weight compound preferably is non-swellable or difficultly swellable. The excipient is preferably amorphous on the balloon 30. The excipient including the water-soluble low-molecular weight compound has an effect of uniformly dispersing the water-insoluble drug on the outer surface of the balloon 30. The excipient constituting the base layer 41 is preferably not a hydrogel. The base layer 41 is rapidly dissolved without being swelled upon contact with an aqueous solution because the base layer 41 is a low-molecular weight compound. The crystal particles of the water-insoluble drug on the outer surface of the balloon 30 becomes easily releasable because the base layer 41 becomes easily soluble upon inflation of the balloon 30 in a blood vessel. The base layer 41 thus increases the amount of the drug crystal particles adhered to the blood vessel. When the base layer 41 is a matrix composed of a contrast agent such as Ultravist (registered trademark), the crystal particles are embedded in the matrix, and crystals are not produced to extend from the substrate of the balloon 30 toward the outside of the matrix. On the other hand, the elongate bodies 42 according to the present embodiment extend from the surface of the substrate of the balloon 30 to the outside of the base layer 41. The length of that portion of the elongate body 42 which is located on the outside of the base layer 41 is greater than the length of that portion of the elongate body 42 which is located inside the base layer 41 (i.e., the portion of the elongate body 42 that protrudes beyond the outer surface of the base layer 41 is longer than the portion of the elongate body 42 that is embedded within the base layer 41).

The base layer 41 is formed to support the base portions 45 of the elongate bodies 42 which are crystals.

The organic solvent is not particularly limited. Examples of the organic solvent include tetrahydrofuran, acetone, glycerin, ethanol, methanol, dichloromethane, hexane, and ethyl acetate. Among these, mixed solvents of some of tetrahydrofuran, ethanol, and acetone are preferable.

Examples of a mixture of an organic solvent with water include a mixture of tetrahydrofuran and water, a mixture of tetrahydrofuran and ethanol and water, a mixture of tetrahydrofuran and acetone and water, a mixture of acetone and ethanol and water, and a mixture of tetrahydrofuran and acetone and ethanol and water.

A method of forming crystals of the water-insoluble drug on the outer surface of the balloon 30 by use of the balloon coating apparatus 50 will be described below.

First, the inflation fluid is supplied into the balloon 30 through the three-way cock connected to the proximal opening portion 27 of the balloon catheter 10 to inflate the balloon 30. Next, the three-way cock is operated to seal up the inflation lumen 23 while the balloon 30 is inflated, thereby maintaining the balloon 30 in the inflated state. The balloon 30 is inflated with a pressure (e.g., 4 atm) lower than a pressure (e.g., 8 atm) at the time of use in a blood vessel in a living body. The coating layer 40 can also be formed on the outer surface of the balloon 30 without inflating the balloon 30. In that case, it is unnecessary to supply the inflation fluid into the balloon 30.

Subsequently, the balloon catheter 10 is rotatably disposed on the support base 70, and the hub 26 is connected to the rotation mechanism section 60 while the dispensing tube 94 is positioned to not contact the outer surface of the balloon 30.

The position of the movable base 81 is next adjusted to position the dispensing tube 94 relative to the balloon 30. The dispending tube 94 is first positioned on the most distal side in a surface region of the balloon 30 where the coating layer 40 is to be formed. As an example, the extending direction (discharge direction) of the dispensing tube 94 is opposite to the rotating direction of the balloon 30. Therefore, at the position where the dispensing tube 94 is put in contact with the balloon 30, the balloon 30 is rotated in the direction opposite to the discharge direction in which the coating solution is discharged from the dispensing tube 94. This rotation opposite to the discharge direction gives a physical stimulus to the coating solution, whereby formation of crystal nuclei of the drug crystal can be promoted. The crystals of the water-insoluble drug formed on the outer surface of the balloon 30 are liable (likely) to be formed assuming a morphological form wherein the crystals include a plurality of elongate bodies 42 having mutually independent long axes because the extending direction (discharge direction) of the dispensing tube 94 toward the opening portion 95 is opposite to the rotating direction of the balloon 30. The extending direction of the dispensing tube 94 may not necessarily be opposite to the rotating direction of the balloon 30. The extending direction of the dispensing tube 94 may be the same as or perpendicular to the rotating direction.

The coating solution is then supplied to the dispensing tube 94 while adjusting the feed rate by the feed pump 93, the balloon catheter 10 is rotated by the rotation mechanism section 60, and the movable base 81 is moved so that the dispensing tube 94 is gradually moved proximally along the axial direction of the balloon 30. The coating solution discharged from the opening portion 95 of the dispensing tube 94 is applied to the outer surface of the balloon 30 to apply the coating solution in a spiral shape, since the dispensing tube 94 is moved relative to the balloon 30 in the axial direction of the balloon 30.

The moving speed of the dispensing tube 94 is not particularly limited, and is, for example, 0.01 to 2 mm/second, preferably 0.03 to 1.5 mm/second, and more preferably 0.05 to 1.0 mm/second. The discharge rate of the coating solution from the dispensing tube 94 is not particularly limited, and is, for example, 0.01 to 1.5 μL/second, preferably 0.01 to 1.0 μL/second, and more preferably 0.03 to 0.8 μL/second. The rotation speed of the balloon 30 is not particularly limited, and is, for example, 10 to 300 rpm, preferably 30 to 250 rpm, and more preferably 50 to 200 rpm. The diameter of the balloon 30 when the balloon 30 is coated with the coating solution is not particularly limited, and is, for example, 1 to 10 mm, and preferably 2 to 7 mm.

Thereafter, the organic solvent contained in the coating solution applied to the outer surface of the balloon 30 volatilizes earlier than water. The organic solvent thus volatilizes in a condition where the water-insoluble drug, the water-soluble low-molecular weight compound and water are left on (retained on) the outer surface of the balloon 30. When the organic solvent thus volatilizes with water left in the coating, the water-insoluble drug is precipitated inside the water-soluble low-molecular weight compound that contains water, and crystals gradually grow from crystal nuclei. This induces the drug crystals of a morphological form wherein the crystals include a plurality of elongate bodies 42 having mutually independent long axes to form on the outer surface of the balloon 30. The base portions 45 of the elongate bodies 42 are located on the outer surface of the balloon 30, on the outer surface of the base layer 41, or in the interior of the base layer 41 (as illustrated in FIG. 4). After the organic solvent has volatilized and the drug crystals are precipitated into the plurality of elongate bodies 42, water evaporates more slowly than the organic solvent, and the base layer 41 including the water-soluble low-molecular weight compound is formed. The time taken for evaporation of water is appropriately set in accordance with the kind of the drug, the kind of the water-soluble low-molecular weight compound, the kind of the organic solvent, the ratios of the amounts of the materials, the coating amount of the coating solution, and the like. The time for the evaporation of water is, for example, approximately 1 to 600 seconds.

The dispensing tube 94 is then gradually moved in the axial direction of the balloon 30 while the balloon 30 is rotated by the rotation mechanism section 60, whereby the coating layer 40 is gradually formed on the outer surface of the balloon 30 along the axial direction of the balloon 30. After the coating layer 40 including the elongate bodies 42 is formed over the whole range of coating for the balloon 30, the rotation mechanism section 60, the movement mechanism section 80, and the application mechanism section 90 operations are stopped.

The balloon catheter 10 is then removed from the balloon coating apparatus 50, which completes the coating of the balloon 30. Thereafter, the inflation fluid is discharged from the balloon 30, whereby the balloon 30 is deflated and folded. Next, the balloon 30 is covered with the tubular protective sheath 15 (see FIG. 1) to complete the manufacture of the balloon catheter 10. The protective sheath 15 is a member for inhibiting the drug from falling off (i.e., being scraped off or removed from) the balloon 30. The protective sheath 15 is removed before the expansion of the balloon 30 of the balloon catheter 10.

A method of using the balloon catheter 10 according to an embodiment of the disclosure will be described below. The method will be described in relation to an example case of treating a stenosed part in a blood vessel in a living body.

First, the operator percutaneously punctures a blood vessel and places an introducer (not shown) indwelling by a known method such as Seldinger method. Next, the protective sheath 15 is removed from the balloon catheter 10, priming is performed, and a guide wire 200 (see FIG. 7) is inserted into the guide wire lumen 24. In this state, the guide wire 200 and the balloon catheter 10 are inserted into the blood vessel through the inside of the introducer. The balloon catheter 10 is subsequently moved forward along the guide wire 200, and the balloon 30 is delivered to a stenosed part 300 in the living body. A guiding catheter may instead be used for delivering the balloon catheter 10 to the stenosed part 300.

Figure 7:
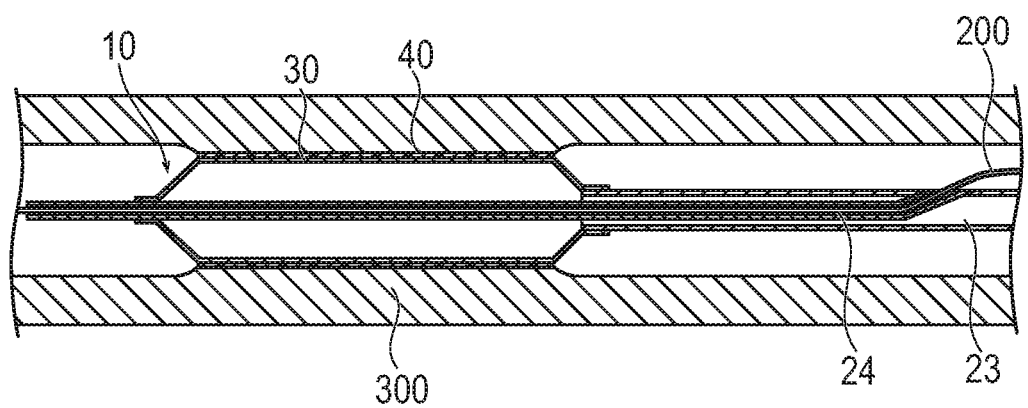
FIG. 7 is a sectional view showing the stenosed part of a blood vessel being pushed wide open by the balloon catheter.

A predetermined quantity of an inflation fluid is next injected into the proximal opening portion 27 of the hub 26 by use of an indeflator or syringe or the like, and the inflation fluid is fed through the inflation lumen 23 into the balloon 30. As shown in FIG. 7, the folded balloon 30 is inflated by injecting the inflation fluid, and the stenosed part 300 is pushed wide open by the balloon 30 (i.e., the balloon 30 expands to and applies a force to expand/widen the stenosed part 300). The coating layer 40 containing the drug crystals provided on the outer surface of the balloon 30 thus makes contact with the stenosed part 300.

When the balloon 30 is inflated and the coating layer 40 is thereby pressed against the living body tissue, the base layer 41 composed of the water-soluble low-molecular weight compound contained in the coating layer 40 is dissolved relatively slowly or relatively rapidly. During the dissolution, the drug is delivered to the living body tissue. Since the first elongate bodies 42A, the second elongate bodies 42B, and the third elongate bodies 42C (which are crystals of the drug) differ in the position of their base portions 45 relative to the base layer 41, these elongate bodies 42A, 42B and 42C differ in tissue deliverability as the base layer 41 is dissolved gradually or rapidly. The inflation of the balloon 30 also causes cracking of the base layer 41, which facilitates dissolution of the base layer 41. This cracking helps enable the elongate bodies 42 as the drug crystals to be easily released from the base layer 41. For this reason, where the first elongate bodies 42A, the second elongate bodies 42B and the third elongate bodies 42C differing in solubility are provided by adjusting the positions of the base portions 45 of the elongate bodies 42, the deliverability of the drug can be arbitrarily set.

The inflation fluid is then discharged by drawing the inflation fluid out via the proximal opening portion 27 of the hub 26, whereby the balloon 30 is deflated and put into a folded state. The guide wire 200 and the balloon catheter 10 are then withdrawn out of the blood vessel through the introducer, to complete the procedure.

As has been described above, the balloon catheter 10 according to this embodiment includes a plurality of elongate bodies 42 on the outer surface of the balloon 30. The plurality of elongate bodies 42 are the crystals of the water-insoluble drug extending while having independent long axes. The balloon catheter 10 has the base layer 41 including the water-soluble low-molecular weight compound disposed in a layer form on the outer surface of the balloon 30. At least part of some of the elongate bodies 42 is located in the inside of the base layer 41. In the balloon catheter 10 configured in this manner, inflation of the balloon 30 causes cracking of the base layer 41. Cracking of the base layer 41 facilitates dissolution of the base layer 41, thereby enabling the elongate bodies 42 as the drug crystals to be easily released from the base layer 41, so that the drug can be effectively delivered to the living body tissue. While the base layer 41 including the water-soluble low-molecular weight compound is dissolved gradually or rapidly, the elongate bodies 42 inside the base layer 41 make contact with the living body tissue. The drug is thus delivered to the living body tissue. The deliverability of the drug can also thus be controlled by the material and thickness of the base layer 41 and the positions of the base portions 45 of the elongate bodies 42 relative to the base layer 41.

The elongate bodies 42 include the first elongate bodies 42A that have their base portions 45 separate from the outer surface of the balloon 30 and located in the interior of the base layer 41. This positioning of the base portions 45 of the first elongate bodies 42A helps ensure that the deliverability of the drug to the living body tissue can be controlled through utilization of the time taken for dissolution of the base layer 41 including the water-soluble low-molecular weight compound.

The elongate bodies 42 include the second elongate bodies 42B extending from the outer surface of the balloon 30. This positioning of the base portions 45 of the second elongate bodies 42B to protrude from the outer surface of the balloon 30 helps ensure that the second elongate bodies 42B are slowly eluted from the base layer 41 as the base layer 41 including the water-soluble low-molecular weight compound is dissolved. The drug can thus be slowly (i.e., relatively slowly) delivered to the living body tissue.

The elongate bodies 42 also include the third elongate bodies 42C extending from the outer surface of the base layer 41 toward the outside of the surface. This positioning of the base portion 45 of the elongate bodies 42C to extend from the outer surface of the base layer 41 helps ensure that the third elongate bodies 42C as a whole immediately make contact with the living body tissue. The drug can thus be instantaneously delivered to the living body tissue in this configuration.

The water-insoluble drug may be rapamycin, paclitaxel, docetaxel, or everolimus. Restenosis of a stenosed part in a blood vessel can be favorably inhibited by the elongate bodies 42 when these drugs are utilized.

The method of manufacturing the balloon catheter 10 according to the present embodiment is a method of manufacturing the balloon catheter 10 including the plurality of elongate bodies 42 being on the outer surface of the balloon 30. The plurality of elongate bodies 42 are crystals of the water-insoluble drug extending while having independent long axes. The manufacturing method includes: the step of supplying a coating solution containing the drug, a water-soluble low-molecular weight compound, an organic solvent and water from the dispensing tube 94 for supplying the coating solution, while keeping the dispensing tube 94 in contact with the outer surface of the balloon 30, and giving a physical stimulus to the coating solution to cause formation of crystal nuclei of the water-insoluble drug; the step of volatilizing the organic solvent while leaving water to cause growth of the elongate bodies 42 on the basis of the crystal nuclei; and the step of evaporating water to form the base layer 41 including the water-soluble low-molecular weight compound. The organic solvent volatilizes from the layer of the water-soluble low-molecular weight compound containing water, whereby the drug crystals grow from the crystal nuclei, and the elongate bodies 42 can be formed so that at least part of the elongate bodies 42 is located in the interior of the base layer 41.

The present disclosure also includes the treatment method (therapeutic method) for delivering a drug to a lesion affected area in a body lumen by use of the balloon catheter 10 described above. The treatment method includes: the step of inserting the balloon 30 into the body lumen and delivering the balloon 30 to the lesion affected area; the step of inflating the balloon 30 to press the balloon 30 against the living body tissue and to bring the elongate bodies 42 into contact with the living body tissue while dissolving the base layer 41 including the water-soluble low-molecular weight compound; and the step of deflating the balloon 30 and withdrawing the balloon 30 out of the body lumen. The inflation of the balloon 30 causes cracking of the base layer 41, which facilitates dissolution of the base layer 41, thereby enabling the elongate bodies 42 as the drug crystals to be easily released from the base layer 41. This process allows the drug to be effectively delivered to the living body tissue. Furthermore, while the base layer 41 including the water-soluble low-molecular weight compound is dissolved gradually or rapidly, the elongate bodies 42 in the interior of the base layer 41 make contact with the living body tissue, and the drug is delivered to the living body tissue. Therefore, the deliverability of the drug can be controlled by the material and thickness of the base layer 41 and the positions of the base portions 45 of the elongate bodies 42 in relation to the base layer 41.

The present disclosure is not limited to any specific embodiment, and various modifications can be made by those skilled in the art within the technical thought of the present disclosure. For example, although the balloon catheter 10 according to the above-described embodiment is of the rapid exchange type, the balloon catheter may be of the over-the-wire type.

Figure 8:
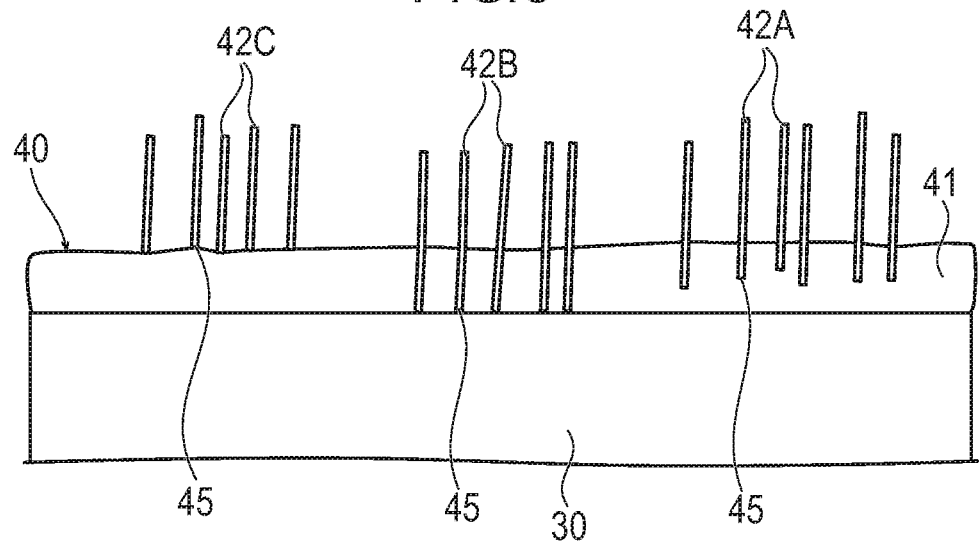
FIG. 8 is a view showing a base layer in a film-formed amorphous state.
Figure 9:
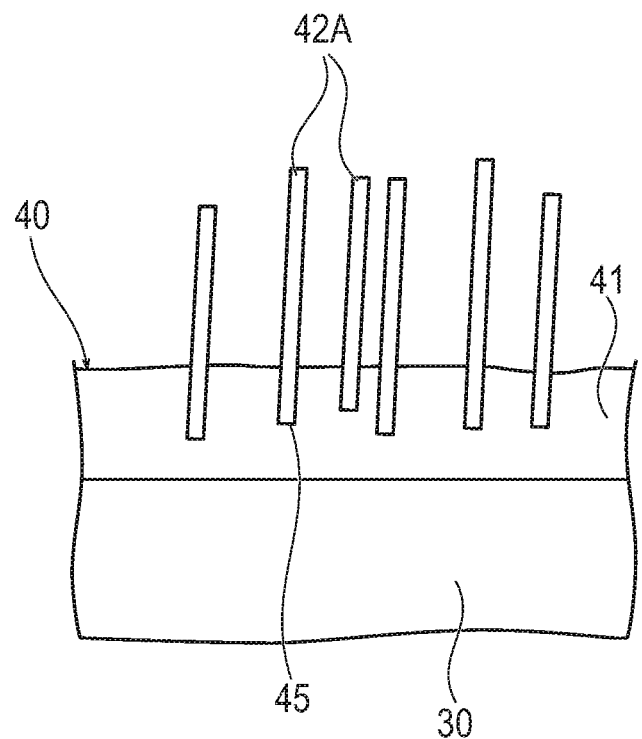
FIG. 9 is a schematic view of the first elongate bodies and the base layer on the outer surface of the balloon.
Figure 10:
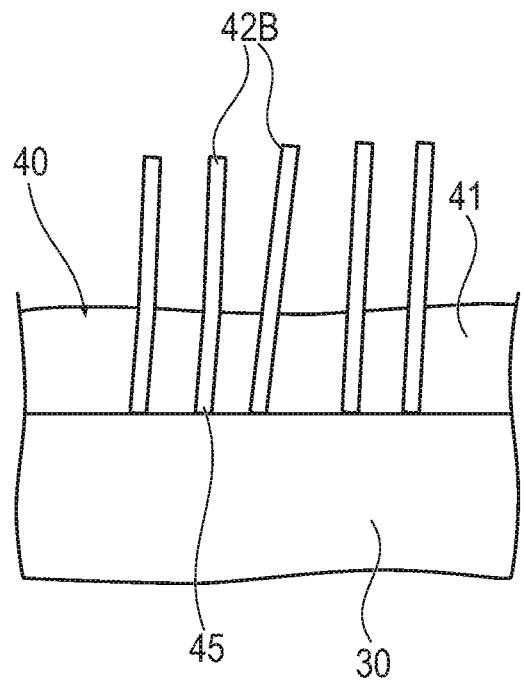
FIG. 10 is a schematic view of the second elongate bodies and the base layer on the outer surface of the balloon.
Figure 11:
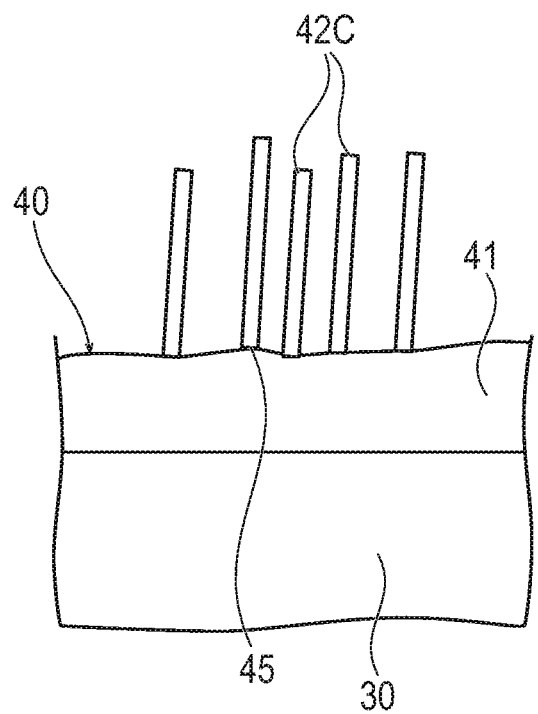
FIG. 11 is a schematic view of the third elongate bodies and the base layer on the outer surface of the balloon.

The base layer 41 is described above as existing as an amorphous phase, crystal particles, or a mixture thereof. While the base layer 41 shown in FIG. 4 is in the state of crystal particles and/or particulate amorphous portions, the base layer 41 may also be in a film-formed amorphous state as illustrated in FIG. 8. The first elongate bodies 42A can extend from the inside of the base layer 41 to the outside of the base layer 41 as shown in FIG. 9. The second elongate bodies 42B extend from the outer surface of the balloon 30 to the outside of the base layer 41 by penetrating the base layer 41 as shown in FIG. 10. As shown in FIG. 11, the third elongate bodies 42C extend from the outer surface of the base layer 41 toward the outside of the surface.

Figure 12:
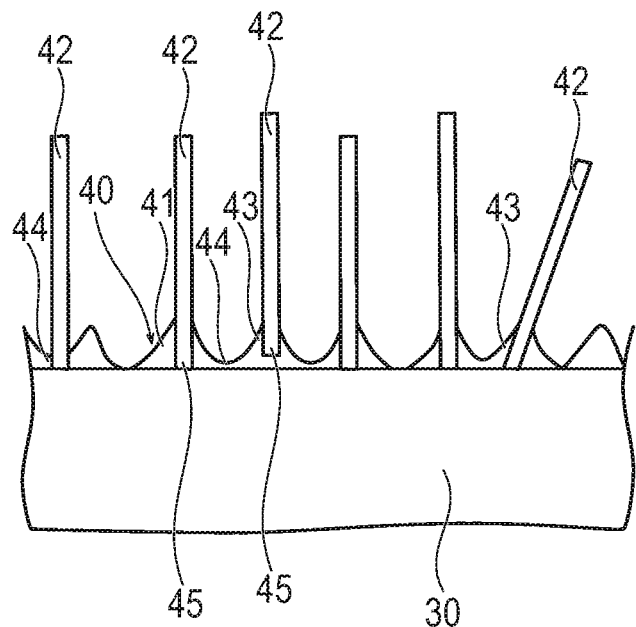
FIG. 12 is a schematic view showing elongate bodies and a base layer on an outer surface of a balloon.

The base layer 41 may also be an additive layer that has a rugged pattern (recesses and projections) as illustrated in FIG. 12. The height of the rugged pattern is 0.1 to 5 μm. The elongate bodies 42 as crystals project from projected portions 43 constituting the rugged pattern of the base layer 41. In other words, the projected portions 43 of the base layer 41 support the elongate bodies 42 as the crystals (i.e., the base portion 45 of the elongate bodies 42 may be positioned in the interior of the projected portions 43 of the base layer 41 as shown in FIG. 12). The base layer 41 may include projected portions 43 from which the elongate bodies 42 do not project. The elongate bodies 42 as the crystals may project from recessed portions 44 constituting the rugged pattern of the base layer 41. The base layer 41 may include both projected portions 43 that support the elongate bodies 42 and projected portions 43 that do not support the elongate bodies 42. The base layer 41 may include both the recessed portions 44 that support the elongate bodies 42 and the recessed portions 44 that do not support the elongate bodies 42. The base layer 41 may also include both the projected portions 43 that support the elongate bodies 42 and the recessed portions 44 that support the elongate bodies 42. The elongate bodies 42 may project obliquely from the base layer 41 such as to be inclined relative to the outer surface of the balloon 30 (e.g., as illustrated by one of the elongate bodies 42 shown in FIG. 12). The base layer 41 may have both the elongate bodies 42 that are substantially perpendicular to the outer surface of the balloon 30 and the elongate bodies 42 that are inclined relative to the outer surface of the balloon 30. The base portions 45 of the elongate bodies 42 may directly contact the outer surface of the balloon 30. Alternatively, the base portions 45 of the elongate bodies 42 may not be in contact with the outer surface of the balloon 30 but may be located within the interior of the base layer 41. The base layer 41 may have both the elongate bodies 42 that are in direct contact with the outer surface of the balloon 30 and the elongate bodies 42 that are not in direct contact with the outer surface of the balloon 30.

Figure 13:
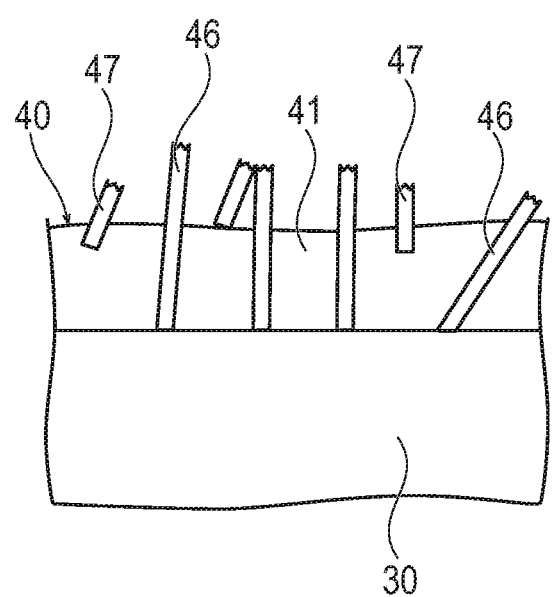
FIG. 13 is a schematic view showing fixed-side elongate bodies and separate-side elongate bodies as well as a base layer on an outer surface of a balloon.

As illustrated in FIG. 13, the crystals may include fixed-side elongate bodies 46 (balloon substrate contacting crystal particles) that originally project from the outer surface of the balloon 30 and separate-side elongate bodies 47 (balloon substrate non-contacting crystal particles or crystal particles that do not directly contact the outer surface of the balloon 30) that are separate from the fixed-side elongate bodies 46. The amount of the fixed-side elongate bodies 46 is greater than the amount of the separate-side elongate bodies 47. The separate-side elongate bodies 47 are formed by being separated from the fixed-side elongate bodies 46 upon breaking of the elongate crystals when the balloon 30 is folded in the manner of being wrapped around the inner tube 22. Of the separate-side elongate body 47, at least part of a distal portion, a proximal portion, and a portion between the distal portion and the proximal portion is in contact with the base layer 41. Part of the separate-side elongate body 47 may be embedded in the base layer 41. The presence of the base layer 41 ensures that the fixed-side elongate bodies 46 and the separate-side elongate bodies 47 are prevented from easily falling off (i.e., being removed from) the outer surface of the balloon 30 during transportation by interactions with the base layer 41. The fixed-side elongate bodies 46 and the separate-side elongate bodies 47 are easily released through dissolution of the base layer 41 when the balloon 30 is inflated and the base layer 41 comes into contact with water (blood). The fixed-side elongate bodies 46 and the separate-side elongate bodies 47, which differ in form from one another, are also different in releasing properties. This difference in releasing properties is preferable from the viewpoint of action on the living body. The fixed-side elongate bodies 46 may be formed by breaking the crystal or may be formed without breaking the crystal. The base layer 41 may have both the fixed-side elongate bodies 46 that are formed by breaking the crystal and the fixed-side elongate bodies 46 that are formed without breaking the crystal. The fixed-side elongate bodies 46 may be standing (extending or protruding) from the base layer 41 (i.e., distally beyond the base layer 41 towards the surrounding environment) or may be lying along the base layer 41. The base layer 41 may have both the fixed-side elongate bodies 46 that are standing from the base layer 41 and the fixed-side elongate bodies 46 that are lying along the base layer 41.

The length of the crystals fixed to the base layer 41, before breaking of crystal, is, for example, 5 to 20 μm. The length after breaking the crystal is, for example, 3 to 20 μm. The length of the fixed-side elongate bodies 46 formed through breaking of crystal is, for example, 5 to 20 μm. The length of the separate-side elongate bodies 47 is, for example, 3 to 10 μm.

Note that the present application is based on Japanese Patent Application No. 2016-058030 filed on Mar. 23, 2016, the contents of which are incorporated herein by reference in entirety thereof.

The detailed description above describes a balloon catheter, balloon catheter manufacturing method and treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
   an elongated main body extending in an axial direction;
   a balloon connected to the elongated main body, the balloon possessing an outer surface and an interior, the balloon being inflatable and deflatable;
   a base layer comprising a non-swellable water-soluble low-molecular weight compound possessing a molecular weight of 50 to 2000 so as to cause the base layer to dissolve without swelling upon contact with an aqueous solution, and formed on the outer surface of the balloon to cover at least a portion of the outer surface of the balloon, the base layer comprising an outer-most exposed surface, an inner-most surface, and an interior between the outer-most exposed surface and the inner-most surface, the inner-most surface being directly on the outer surface of the balloon; and
   a plurality of elongate bodies extending radially away from the outer surface of the balloon, the plurality of elongate bodies being crystals of a water-insoluble drug,
   wherein each elongate body of the plurality of elongate bodies possesses an independent longitudinal axis, a proximal end, and a distal end which protrudes beyond the outer-most exposed surface of the base layer, the proximal ends of some of the plurality of elongate bodies contacting the outer surface of the balloon, and the proximal ends of others of the plurality of elongate bodies not contacting the outer surface of the balloon.

2. The balloon catheter according to claim 1, wherein the water-insoluble drug is rapamycin, paclitaxel, docetaxel, or everolimus.

3. The balloon catheter according to claim 1, wherein a collective volume of the plurality of elongate bodies is larger than a volume of the base layer on the outer surface of the balloon.

4. The balloon catheter according to claim 1, wherein the base layer is formed of crystal particles.

5. The balloon catheter according to claim 1, wherein the non-swellable water-soluble low-molecular weight compound is an excipient that is not a hydrogel and that is not a matrix.

6. The balloon catheter according to claim 1, wherein the non-swellable water-soluble low-molecular weight compound is an excipient that has an effect of uniformly dispersing the water-insoluble drug on the outer surface of the balloon.

7. The balloon catheter according to claim 1, wherein the base layer possesses a rugged pattern of recesses and projections having a height of 0.1 to 5 µm.

8. The balloon catheter according to claim 1, wherein the longitudinal axis of each of the plurality of elongate bodies has an inclination angle with respect to the outer surface in the range of 45 to 135 degrees.

9. A method of coating a balloon catheter comprising:
   causing a balloon catheter to contact a dispensing tube, the balloon catheter comprising an elongated tubular body which possesses a distal portion and a balloon attached to the distal portion of the elongated tubular body, the balloon possessing an outer surface that contacts the dispensing tube;
   applying a coating solution containing a water-insoluble drug, a non-swellable water-soluble low-molecular weight compound possessing a molecular weight of 50 to 2000 so as to cause a base layer formed therefrom to dissolve without swelling upon contact with an aqueous solution, an organic solvent, and water from the dispensing tube onto the outer surface of the balloon of the balloon catheter, the coating solution being applied by the dispensing tube while keeping the dispensing tube in contact with the outer surface of the balloon;
   giving a physical stimulus to the coating solution to cause formation of crystal nuclei of the water-insoluble drug while applying the coating solution with the dispensing tube;
   volatilizing the organic solvent while leaving the water to cause growth of a plurality of elongate bodies based on the crystal nuclei;
   evaporating the water to form the base layer on the outer surface of the balloon, the base layer including the non-swellable water-soluble low-molecular weight compound, the base layer comprising an outer-most exposed surface, an inner-most surface, and an interior between the outer-most exposed surface and the inner-most surface, the inner-most surface being directly on the outer surface of the balloon; and
   wherein each elongate body of the plurality of elongate bodies possesses an independent longitudinal axis, a proximal end, and a distal end which protrudes beyond the outer-most exposed surface of the base layer, the proximal ends of some of the plurality of elongate bodies contacting the outer surface of the balloon, and the proximal ends of others of the plurality of elongate bodies not contacting the outer surface of the balloon.

10. The method according to claim 9, wherein the physical stimulus includes rotating the balloon catheter relative to the dispensing tube.

11. The method according to claim 10, wherein
   the applying of the coating solution from the dispensing tube is in a dispensing direction;
   the balloon catheter rotates in a rotating direction; and
   the rotating direction of the balloon catheter is opposite the dispensing direction.

12. The method according to claim 9, wherein the evaporating of the water forms the base layer in a rugged pattern on the outer surface of the balloon, the rugged pattern comprising recesses and projections.

13. The method according to claim 12, wherein the growth of the plurality of elongate bodies based on the crystal nuclei occurs at a location of the projections of the rugged pattern of the base layer.

14. The method according to claim 9, further comprising breaking a distal portion of at least some of the plurality of elongate bodies.

15. The method according to claim 9, wherein the base layer possesses a rugged pattern of recesses and projections having a height of 0.1 to 5 µm.

16. The method according to claim 9, wherein the longitudinal axis of each of the plurality of elongate bodies has an inclination angle with respect to the outer surface in the range of 45 to 135 degrees.

17. A treatment method for delivering a drug to a lesion affected area in a body lumen of a living body, the treatment method comprising:

introducing a balloon catheter into the living body, the balloon catheter comprising an elongated tubular body, a balloon attached to a distal portion of the elongated tubular body, a base layer 1) comprising a non-swellable water-soluble low-molecular weight compound possessing a molecular weight of 50 to 2000 so as to cause the base layer to dissolve without swelling upon contact with an aqueous solution and 2) located on an outer surface of the balloon, and a plurality of elongate bodies extending radially outward through at least part of the base layer, the plurality of elongate bodies being crystals of a water-insoluble drug, the base layer comprising an outer-most exposed surface, an inner-most surface, and an interior between the outer-most exposed surface and the inner-most surface, the inner-most surface being directly on the outer surface of the balloon, wherein each elongate body of the plurality of elongate bodies possesses an independent longitudinal axis, a proximal end, and a distal end which protrudes beyond the outer-most exposed surface of the base layer, the proximal ends of some of the plurality of elongate bodies contacting the outer surface of the balloon, and the proximal ends of others of the plurality of elongate bodies not contacting the outer surface of the balloon;

moving the balloon catheter within the living body into the body lumen to position the balloon of the balloon catheter at the lesion affected area;

inflating the balloon to press the balloon against living body tissue of the lesion affected area, the inflating of the balloon causing the plurality of elongate bodies to contact the living body tissue;

dissolving the base layer including the water-soluble low-molecular weight compound;

deflating the balloon; and withdrawing the balloon catheter out of the living body while the balloon is deflated.

18. The treatment method according to claim 17, wherein the dissolving of the base layer including the water-soluble low-molecular weight compound releases the plurality of elongate bodies from the base layer.

19. The treatment method according to claim 17, further comprising cracking the base layer by the inflating of the balloon.

20. The treatment method according to claim 17, wherein the base layer possesses a rugged pattern of recesses and projections having a height of 0.1 to 5 μm.

21. The treatment method according to claim 17, wherein the longitudinal axis of each of the plurality of elongate bodies has an inclination angle with respect to the outer surface in the range of 45 to 135 degrees.

* * * * *